United States Patent
Chen et al.

(10) Patent No.: US 12,297,188 B2
(45) Date of Patent: May 13, 2025

(54) CRYSTALLINE FORMS OF (S)-1-(1-ACRYLOYLPYRROLIDIN-3-YL)-3-((3,5-DIMETHOXYPHENYL)ETHYNYL)-5-(METHYLAMINO)-1H-PYRAZOLE-4-CARBOXAMIDE

(71) Applicant: Beijing InnoCare Pharma Tech Co., Ltd., Beijing (CN)

(72) Inventors: Xiangyang Chen, Beijing (CN); Jing Feng, Beijing (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 532 days.

(21) Appl. No.: 17/806,796

(22) Filed: Jun. 14, 2022

(65) Prior Publication Data
US 2022/0363669 A1    Nov. 17, 2022

Related U.S. Application Data

(63) Continuation of application No. PCT/CN2020/137963, filed on Dec. 21, 2020.

(60) Provisional application No. 62/953,744, filed on Dec. 26, 2019.

(51) Int. Cl.
C07D 403/04    (2006.01)

(52) U.S. Cl.
CPC ........ *C07D 403/04* (2013.01); *C07B 2200/13* (2013.01)

(58) Field of Classification Search
CPC .... A61P 35/00; C07B 2200/13; C07D 403/04
See application file for complete search history.

(56) References Cited

U.S. PATENT DOCUMENTS 11,572,353 B2 *   2/2023   Chen ................ C07D 231/44
2021/0332027 A1  10/2021   Chen et al.

FOREIGN PATENT DOCUMENTS

| | | |
|---|---|---|
| MX | 2019/003143 A | 6/2019 |
| WO | 2012/098416 | 7/2012 |
| WO | 2012098416 A1 | 7/2012 |
| WO | 2018/049781 | 3/2018 |
| WO | 2018049781 A1 | 3/2018 |
| WO | 2018/064119 | 4/2018 |
| WO | 2018064119 A1 | 4/2018 |

OTHER PUBLICATIONS

Kazuhide Ashizawa, Chemistry of Polymorphism and Crystallization of Pharmaceuticals, 2002, pp. 273, 278, and 305-317, with machine English translation.
Noriaki Hirayama, Handbook of Production of Organic Compound Crystals, 2008, pp. 17-23, 37-40, 45-51, and 57-65, with machine English translation.
Dario Braga, "Crystal Polymorphism and Multiple Crystal Forms", Structure and Bonding, Feb. 2009, pp. 25-50.
Rolf Hilfker et al., "Relevance of Solid-State Properties for Pharmaceutical Products", Polymorphism: in the Pharmaceutical Industry, 2006, pp. 1-19.
International Search Report for PCT Application No. PCT/CN2020/137963. Mail Date: Mar. 23, 2021. 5 pages.
Extended European Search Report for Co-Pending EP Application No. 20904508.7, dated Dec. 11, 2023, 6 pages.
Caira "Crystalline Polymorphism of Organic Compounds" Department of Chemistry, University of Cape Town, Topics in Current Chemistry; [Topics in Current Chemistry], Springer, Berlin, DE, vol. 198, Jan. 1, 1998 (Jan. 1, 1998), 46 pages.
International Search Report for PCT/CN2020/137963, dated Mar. 23, 2021, 5 pages.

\* cited by examiner

*Primary Examiner* — Adam C Milligan
*Assistant Examiner* — Elvie Grace Sellers
(74) *Attorney, Agent, or Firm* — Viola Kung; Perkins Coie LLP (57) ABSTRACT

The present invention relates to various crystalline forms of (S)-1-(1-acryloylpyrrolidin-3-yl)-3-((3,5-dimethoxyphenyl) ethynyl)-5-(methylamino)-1H-pyrazole-4-carboxamide.
The present invention also relates to pharmaceutical compositions comprising the crystalline forms.

6 Claims, 9 Drawing Sheets

CRYSTALLINE FORMS OF (S)-1-(1-ACRYLOYLPYRROLIDIN-3-YL)-3-((3,5-DIMETHOXYPHENYL)ETHYNYL)-5-(METHYLAMINO)-1H-PYRAZOLE-4-CARBOXAMIDE

This application is a continuation of PCT/CN2020/137963, filed Dec. 21, 2020; which claims the benefit of U.S. Provisional Application No. 62/953,744, filed Dec. 26, 2019. The contents of the above-identified applications are incorporated herein by reference in their entireties.

FIELD OF INVENTION

The present invention relates to several crystalline forms of (S)-1-(1-acryloylpyrrolidin-3-yl)-3-((3,5-dimethoxyphenyl)ethynyl)-5-(methylamino)-1H-pyrazole-4-carboxamide.

BACKGROUND OF THE INVENTION (S)-1-(1-acryloylpyrrolidin-3-yl)-3-((3,5-dimethoxyphenyl)ethynyl)-5-(methylamino)-1H-pyrazole-4-carboxamide (Compound I) is a potent inhibitor of fibroblast growth factor receptor (FGFR). The preparation of Compound I and its use in the treatment of cancers are described in WO2018/049781, which is incorporated herein by reference in its entirety.

DETAILED DESCRIPTION OF THE INVENTION

The present invention provides several crystalline forms of (S)-1-(1-acryloylpyrrolidin-3-yl)-3-((3,5-dimethoxyphenyl)ethynyl)-5-(methylamino)-1H-pyrazole-4-carboxamide (Compound I) and the processes for their preparations. The crystalline forms of Compound I are suitable for pharmaceutical research and for preparing a pharmaceutical formulation.

Compound I

Crystalline Form A

The crystalline form A of Compound I can be prepared by crystallizing the starting material Compound I from a solvent mixture of acetone and water. The synthesis of the starting material Compound I is as described in WO2018/049781.

Figure 1:
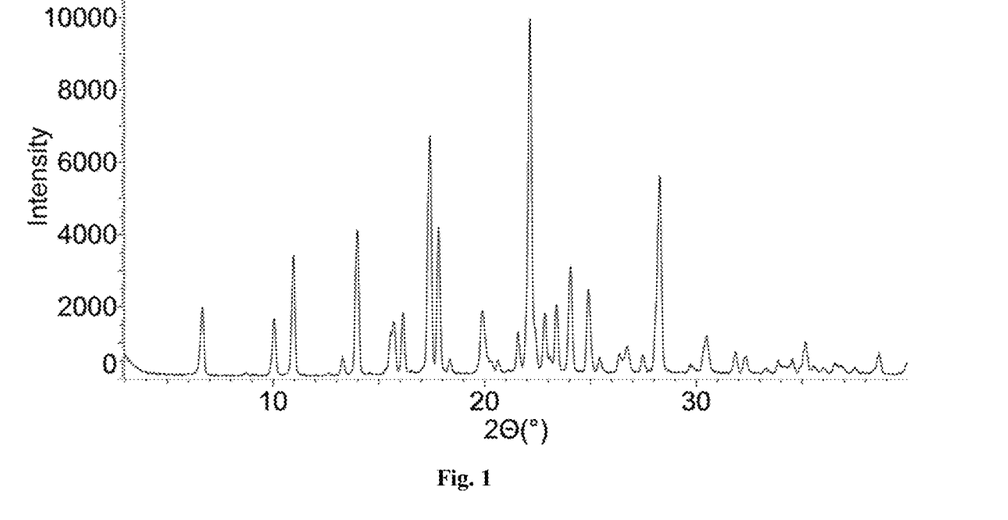
FIG. 1 shows an X-ray powder diffraction (XRPD) diagram of Form A.

The XRPD diagram of Form A is shown in FIG. 1, having characteristic peaks at 2theta values of 22.1°±0.2°, 17.4°±0.2°, 28.3°±0.2°.

Furthermore, the XRPD of Form A further shows one or more characteristic peaks at 2theta values of 17.8°±0.2°, 14.0°±0.2°, 11.0°±0.2°.

Furthermore, the XRPD of Form A further shows one or more characteristic peaks at 2theta values of 24.1°±0.2°, 24.9°±0.2°, 6.7°±0.2°.

The XRPD data of Form A is shown in Table 1.

TABLE 1

| 2theta | d-Spacing | Intensity (%) |
| --- | --- | --- |
| 6.66 | 13.26 | 19.2 |
| 8.69 | 10.17 | 0.6 |
| 10.05 | 8.79 | 16.3 |
| 10.96 | 8.06 | 33.9 |
| 12.62 | 7.01 | 0.8 |
| 13.29 | 6.65 | 5.1 |
| 13.99 | 6.33 | 40.8 |
| 14.55 | 6.08 | 0.5 |
| 15.71 | 5.64 | 14.3 |
| 16.14 | 5.49 | 17.1 |
| 17.42 | 5.09 | 67.0 |
| 17.82 | 4.97 | 41.1 |
| 18.36 | 4.83 | 4.0 |
| 19.90 | 4.46 | 17.6 |
| 20.29 | 4.37 | 3.1 |
| 20.63 | 4.30 | 3.3 |
| 21.58 | 4.11 | 10.9 |
| 22.14 | 4.01 | 100.0 |
| 22.85 | 3.89 | 16.2 |
| 23.40 | 3.80 | 18.7 |
| 24.07 | 3.69 | 29.8 |
| 24.91 | 3.57 | 22.9 |
| 25.43 | 3.50 | 4.1 |
| 26.37 | 3.38 | 5.0 |
| 26.74 | 3.33 | 7.2 |
| 27.48 | 3.24 | 4.9 |
| 28.28 | 3.15 | 55.5 |
| 29.74 | 3.00 | 2.3 |
| 30.50 | 2.93 | 10.3 |
| 31.86 | 2.81 | 6.0 |

TABLE 1-continued

| 2theta | d-Spacing | Intensity (%) |
|---|---|---|
| 32.35 | 2.77 | 4.6 |
| 33.27 | 2.69 | 1.3 |
| 33.88 | 2.64 | 3.4 |
| 34.53 | 2.60 | 3.6 |
| 35.17 | 2.55 | 8.2 |
| 35.55 | 2.52 | 1.8 |
| 36.04 | 2.49 | 1.4 |
| 36.61 | 2.45 | 2.2 |
| 36.83 | 2.44 | 2.0 |
| 37.51 | 2.40 | 1.8 |
| 38.64 | 2.33 | 5.9 |

Form A of Compound I is an anhydride.

Figure 2:
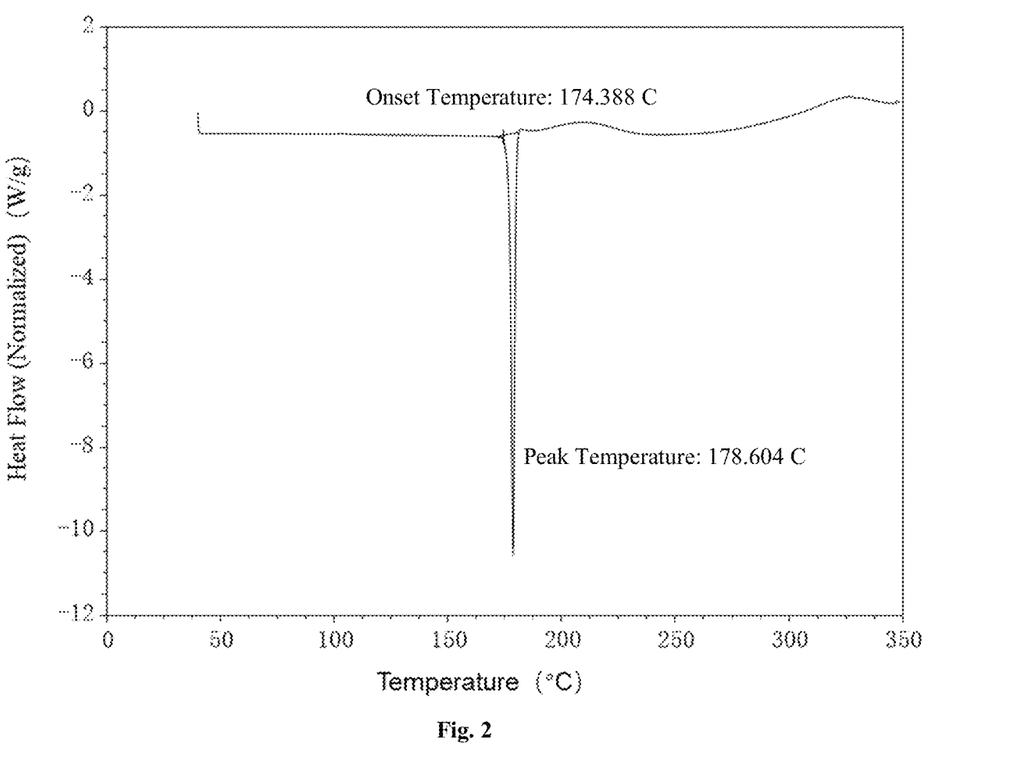
FIG. 2 shows a differential scanning calorimeter (DSC) diagram of Form A.

Form A of Compound I shows an endothermic peak at 178° C. (the peak temperature) when heated in a DSC. The DSC diagram is shown in FIG. 2.

Figure 3:
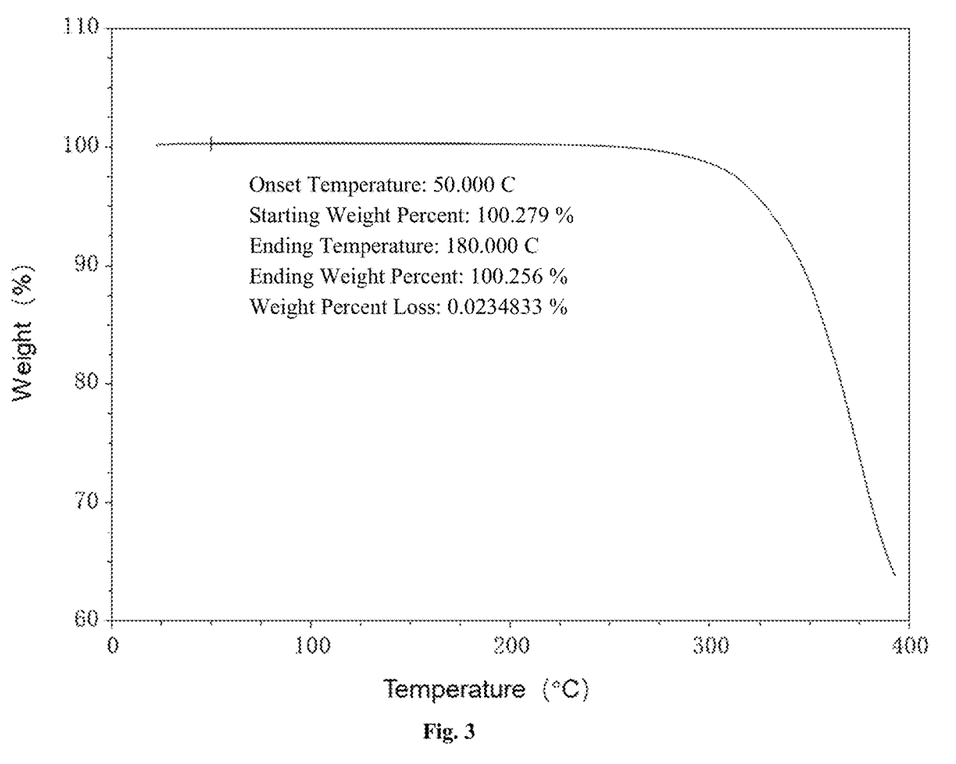
FIG. 3 shows a thermogravimetric analysis (TGA) diagram of Form A.

Form A of Compound I shows about 0.02% weight loss when heated to 180° C. in a thermogravimetric analyzer. The TGA diagram is shown in FIG. 3. TGA is a method of thermal analysis in which the mass of a sample is measured over time as the temperature changes. TGA evaluates the thermal stability of a material. FIG. 3 shows that Form A is thermally stable, with negligible mass change when heated to 180° C.

Form A is stable after storage at 80° C. (closed) for one day, and 25° C./60% RH and 40° C./75% RH (opened) for one week, without changing the characteristic peaks in the XRPD diagram.

Form A of Compound I has a solubility of 6.4 μg/mL after equilibrium in water at room temperature for 24 hours which is classified as almost insoluble or insoluble.

Form A shows a water uptake of 0.14% at 80% RH and is not hygroscopic.

Crystalline Form B

The crystalline form B of Compound I can be prepared by firstly converting Form A into an amorphous form, followed by different preparation methods, such as gas-liquid permeation, volatilization and crystallization.

Figure 4:
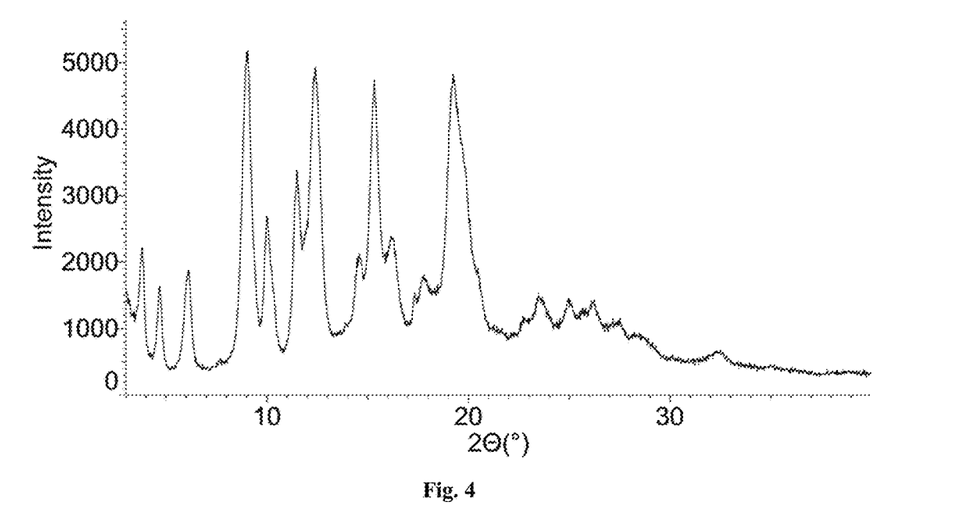
FIG. 4 shows an XRPD diagram of Form B.

The XRPD diagram of Form B is shown in FIG. 4, having characteristic peaks at 2theta values of 9.0°±0.2°, 12.4°±0.2°, 19.3°±0.2°.

Furthermore, the XRPD of Form B further shows one or more characteristic peaks at 2theta values of 15.3°±0.2°, 11.5°±0.2°, 10.0°±0.2°.

Furthermore, the XRPD of Form B further shows one or more characteristic peaks at 2theta values of 6.1°±0.2°, 16.2°±0.2°, 3.8°±0.2°.

The XRPD data of Form B is shown in Table 2.

TABLE 2

| 2theta | d-Spacing | Intensity (%) |
|---|---|---|
| 3.83 | 23.03 | 29.5 |
| 4.68 | 18.86 | 23.3 |
| 6.09 | 14.50 | 31.3 |
| 7.73 | 11.42 | 1.4 |
| 9.04 | 9.77 | 100.0 |
| 10.03 | 8.82 | 43.7 |
| 11.49 | 7.69 | 57.4 |
| 12.40 | 7.13 | 89.3 |
| 14.59 | 6.07 | 24.4 |
| 15.34 | 5.77 | 82.0 |
| 16.19 | 5.47 | 30.2 |
| 17.44 | 5.08 | 8.3 |
| 17.80 | 4.98 | 17.1 |
| 19.25 | 4.61 | 83.5 |

TABLE 2-continued

| 2theta | d-Spacing | Intensity (%) |
|---|---|---|
| 20.46 | 4.34 | 20.9 |
| 22.81 | 3.90 | 6.3 |
| 23.52 | 3.78 | 13.1 |
| 23.61 | 3.77 | 11.3 |
| 24.99 | 3.56 | 10.7 |
| 26.22 | 3.40 | 12.9 |
| 27.46 | 3.25 | 7.8 |

Form B is chemically stable. Form B is not physically stable and it can be converted to Form A or Form C.

Form B has an equilibrium solubility of 15.14 μg/mL, about 2.42% weight loss by TGA, and three endothermic peaks at 70° C., 101° C., 174° C. by DSC.

Form B of Compound I is a hydrate.

Crystalline Form C

The crystalline Form C of Compound I can be prepared from Form B, for example, by heating.

Figure 5:
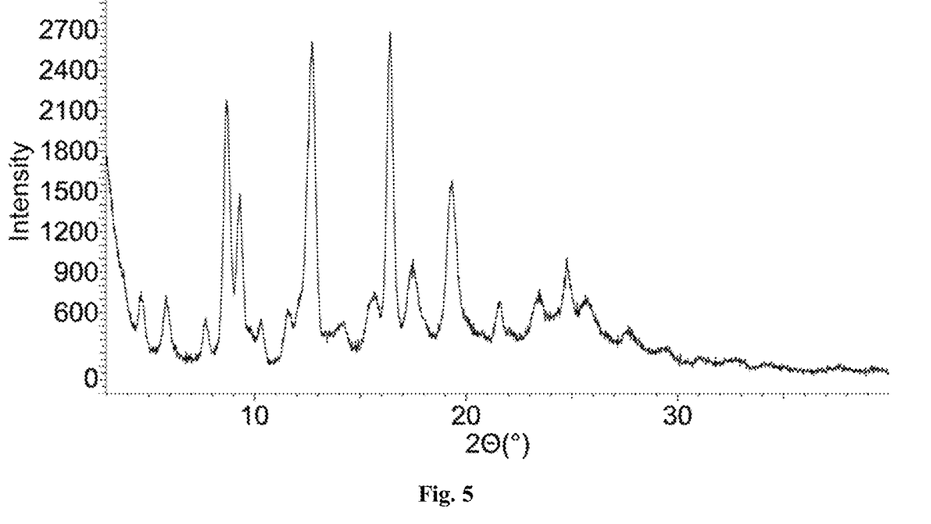
FIG. 5 shows an XRPD diagram of Form C.

The XRPD diagram of Form C is shown in FIG. 5, having characteristic peaks at 2theta values of 12.7°±0.2°, 16.4°±0.2°, 8.7°±0.2°.

Furthermore, the XRPD of Form C further shows one or more characteristic peaks at 2theta values of 9.3°±0.2°, 19.3°±0.2°, 24.8°±0.2°.

Furthermore, the XRPD of Form C further shows one or more characteristic peaks at 2theta values of 17.5°±0.2°, 5.8°±0.2°, 15.7°±0.2°.

The XRPD data of Form C is shown in Table 3.

TABLE 3

| 2theta | d-Spacing | Intensity (%) |
|---|---|---|
| 4.65 | 19.01 | 13.8 |
| 5.81 | 15.19 | 16.7 |
| 7.68 | 11.50 | 13.7 |
| 8.68 | 10.18 | 82.9 |
| 9.31 | 9.49 | 53.2 |
| 10.33 | 8.56 | 12.7 |
| 11.62 | 7.61 | 14.7 |
| 12.72 | 6.95 | 100.0 |
| 14.23 | 6.22 | 8.9 |
| 15.52 | 5.71 | 13.8 |
| 15.66 | 5.65 | 16.6 |
| 16.41 | 5.40 | 99.0 |
| 17.50 | 5.06 | 24.7 |
| 19.33 | 4.59 | 49.7 |
| 21.58 | 4.12 | 10.0 |
| 23.46 | 3.79 | 12.8 |
| 24.76 | 3.59 | 25.2 |
| 25.64 | 3.47 | 13.9 |
| 25.83 | 3.45 | 11.3 |
| 27.61 | 3.22 | 4.7 |
| 29.50 | 3.03 | 2.7 |

Form C of Compound I is a hydrate.

Figure 6:
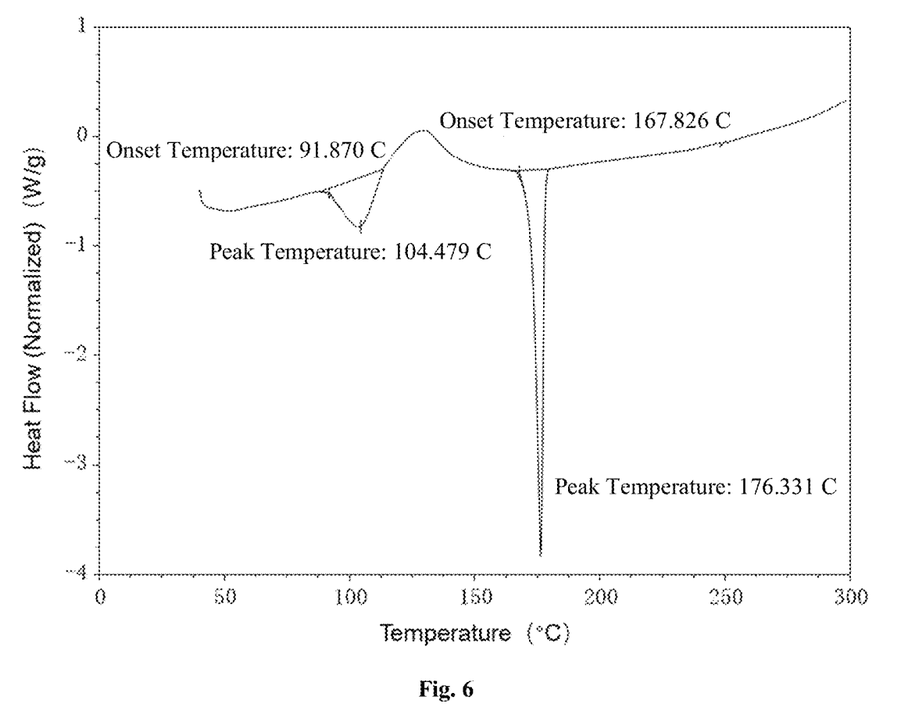
FIG. 6 shows a DSC diagram of Form C.

Form C of Compound I shows two endothermic peaks at 104° C. and 178° C. (the peak temperatures) when heated in a differential scanning calorimeter. The DSC diagram is shown in FIG. 6.

Figure 7:
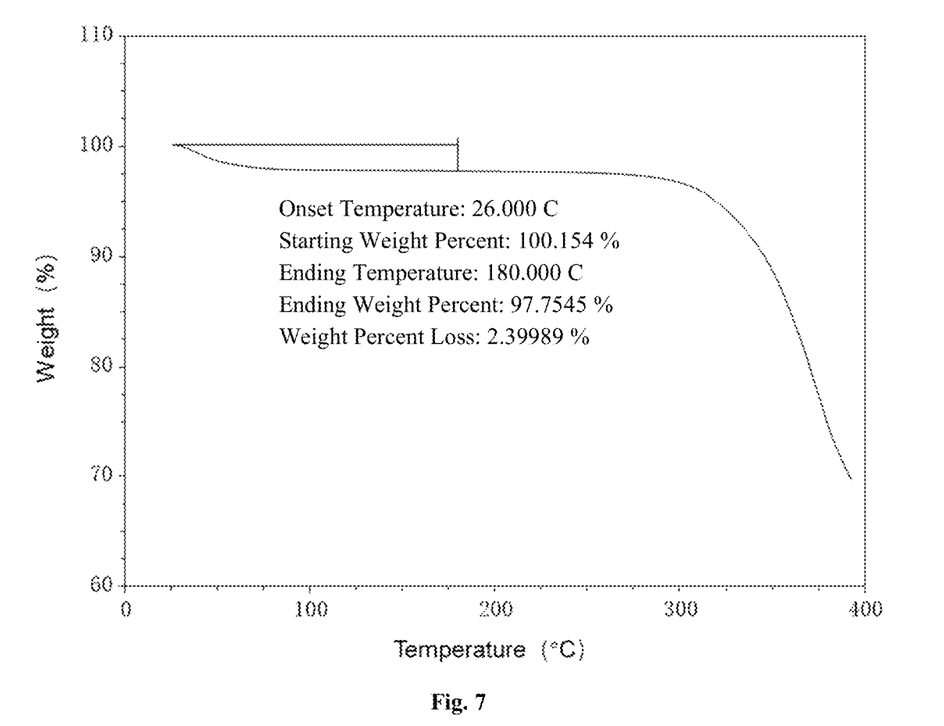
FIG. 7 shows a TGA diagram of Form C.

Form C of Compound I shows about 2.40% weight loss when heated to 180° C. in a thermogravimetric analyzer. The TGA diagram is shown in FIG. 7.

Form C is stable after storage at 25° C./60% RH and 40° C./75% RH (opened) for one week and does not change the characteristic peaks in the XRPD diagram under different humidity conditions.

Form C of Compound I has a solubility of 15.93 μg/mL after equilibrium in water at room temperature for 24 hours which is classified as almost insoluble or insoluble.

Form C is moderately hygroscopic.

Pharmaceutical Composition

The present invention is also directed to a pharmaceutical composition comprising a therapeutically effective amount of Form A, Form B, or Form C, or a mixture thereof, in any ratio, and a pharmaceutically acceptable carrier.

The crystalline Forms A, B and C are useful as an active pharmaceutical ingredient (API) in a pharmaceutical composition, with Forms A and C being preferred, and Form A being more preferred.

The following examples further illustrative the present invention. These examples are intended merely to be illustrative of the present invention and are not to be construed as being limiting.

EXAMPLES

X-ray powder diffraction (XRPD) studies in the present disclosure were performed using a Bruker D8 ADVANCE X-ray powder diffractometer. The parameters of the XRPD method of Compound I were as follows:
X-ray reflection: Cu, Kα
  Kα1 (Å): 1.540598; Kα2 (Å): 1.544426
  Kα2/Kα1 intensity ratio: 0.50
Voltage: 40 kV
Current: 40 mA
Scanning range: from 3.0 to 40.0 degree
Differential scanning calorimetry (DSC) data in the present disclosure were acquired by a TA DSC250. The parameters of the DSC method of Compound I were as follows:
Heating rate: 10° C./min
Purging gas: nitrogen
Thermogravimetric analysis (TGA) data in the present disclosure were acquired by a TA TGA550. The parameters of the TGA method of Compound I were as follows:
Heating rate: 10° C./min
Purging gas: nitrogen
Dynamic vapor sorption (DVS) data in the present disclosure were acquired by a SMS Intrinsic DVS. The parameters of the DVS method of Compound I were as follows:
Temperature: 25° C.
Gas and flow rate: nitrogen, 200 mL/min
dm/dt: 0.002%/min
Relative humidity (RH) range: 0% RH-95% RH Example 1. Preparation of Form A The starting material Compound I (7.5 g) was dissolved in a mixed solvent of acetone (59.6 mL) and deionized water (15.6 mL) at 50° C., and the resulting solution was cooled to 30° C. and stirred for five hours. 20 mL deionized water was then added slowly and stirred for two hours, followed by slow addition of 45 mL deionized water. After additional two hours stirring, the temperature was lowered to 20-25° C., and crystals were precipitated out and filtered. The solid was washed with 15 mL 25% acetone in water twice and dried at 45° C. under vacuum for 18 hours to give 6.65 g of Form A.

The XRPD data of Form A comprising diffraction peaks are listed in Table 1. The XRPD diagram is shown in FIG. 1. The DSC curve is shown in FIG. 2. The TGA curve is shown in FIG. 3.

Example 2. Preparation of Form B

Form A of Compound I was heated to 200° C. and then cooled to room temperature to give an amorphous sample. About 25 mg of the amorphous sample in THF/water (4:1 v/v) was stirred for two hours and filtered. The filtrate was then cooled to 5° C. at 0.1° C./min. The crystals were centrifuged at 10000 rmp for 2 min and dried at room temperature under vacuum overnight to give Form B.

The XRPD data of Form B comprising diffraction peaks are listed in Table 2. The XRPD diagram is shown in FIG. 4.

Example 3. Preparation of Form C

About 30 mg Form B of Compound I was placed in a DVS analyzer with relative humidity changes from 50% RH to 90% RH by every 10% RH increase, and to 95% RH by a 5% RH increase, then to 0% RH, followed by changes to 95% RH in the same manners to give Form C. Form C can also be prepared by heating Form B of Compound I to 70° C. and then cooling to room temperature at a rate of 5-30° C./min.

The XRPD data of Form C comprising diffraction peaks are listed in Table 3. The XRPD diagram is shown in FIG. 5. The DSC curve is shown in FIG. 6. The TGA curve is shown in FIG. 7.

Example 4. Stability Assessment of Form A

Figure 8:
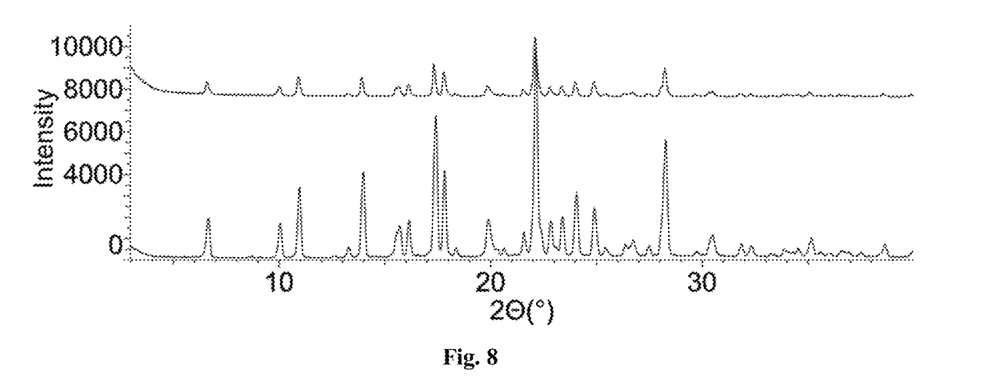
FIG. 8 shows the overlay of XRPD diagrams of Form A before (below) and after (above) stored at 80° C. for one day.
Figure 9:
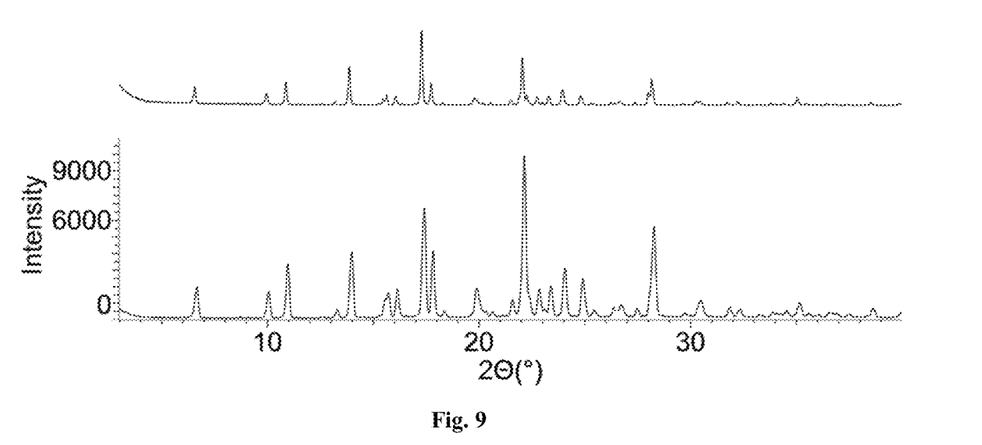
FIG. 9 shows the overlay of XRPD diagrams of Form A before (below) and after (above) stored under 25° C./60% RH for one week.
Figure 10:
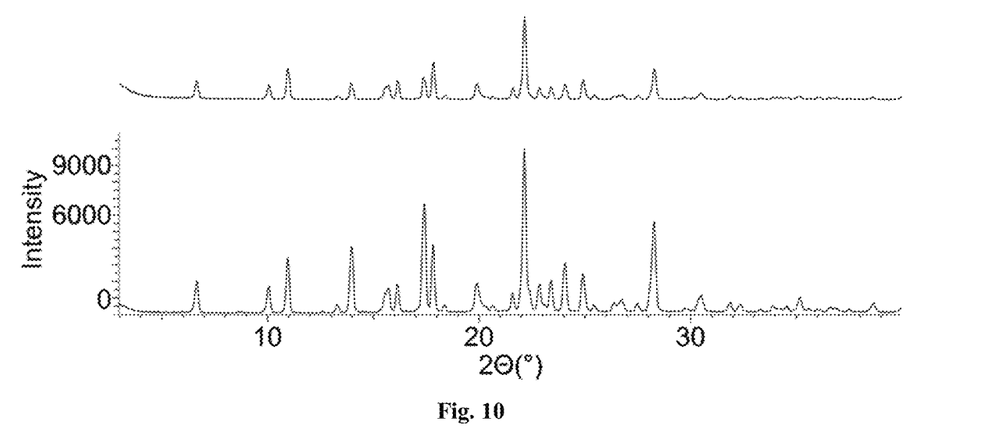
FIG. 10 shows the overlay of XRPD diagrams of Form A before (below) and after (above) stored under 40° C./75% RH for one week.

About 10 mg Form A of Compound I was added to each 1.5-mL glass vial and stored at (i) 80° C. (closed) for one day, or (ii) 25° C./60% RH and 40° C./75% RH (opened) for one week, and then analyzed for XRPD and HPLC purity. The XRPDs are shown in FIGS. 8, 9 and 10 have little or no change. The stability results are shown in Table 4, indicating no purity change neither.

TABLE 4

| | Stability Testing Condition | | | |
|---|---|---|---|---|
| | Day 0 | 80° C. for 1 day | 25° C./60% RH for 1 week | 40° C./75% RH for 1 week |
| Purity (%) | 99.75 | 99.77 | 99.78 | 99.76 |
| Crystalline Form | A | A | A | A |

Example 5. Hygroscopicity Assessment of Form A

Figure 11:
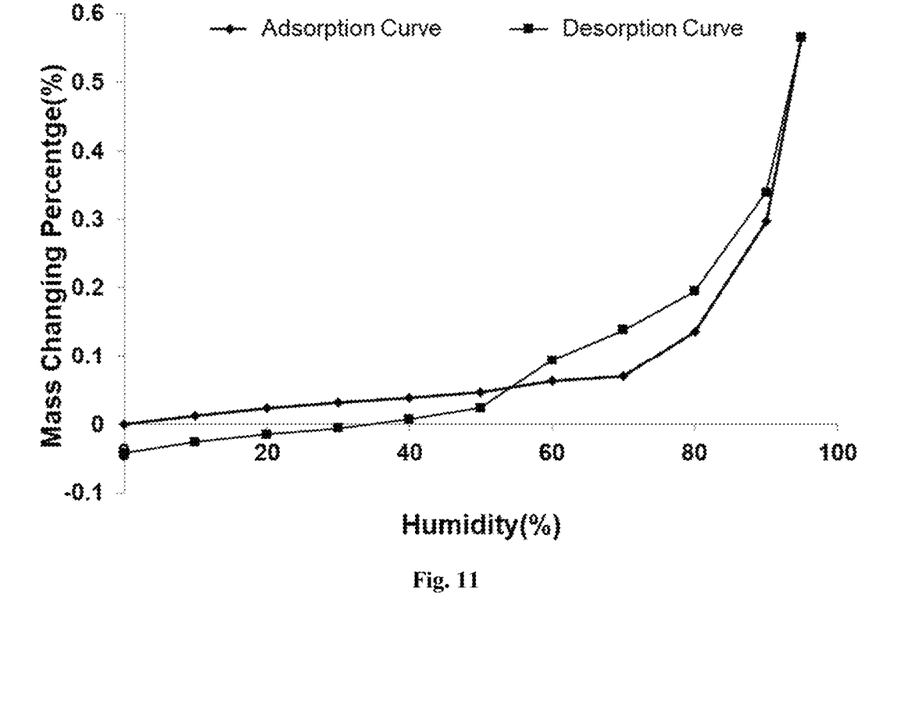
FIG. 11 shows a dynamic vapor sorption (DVS) diagram of Form A.
Figure 12:
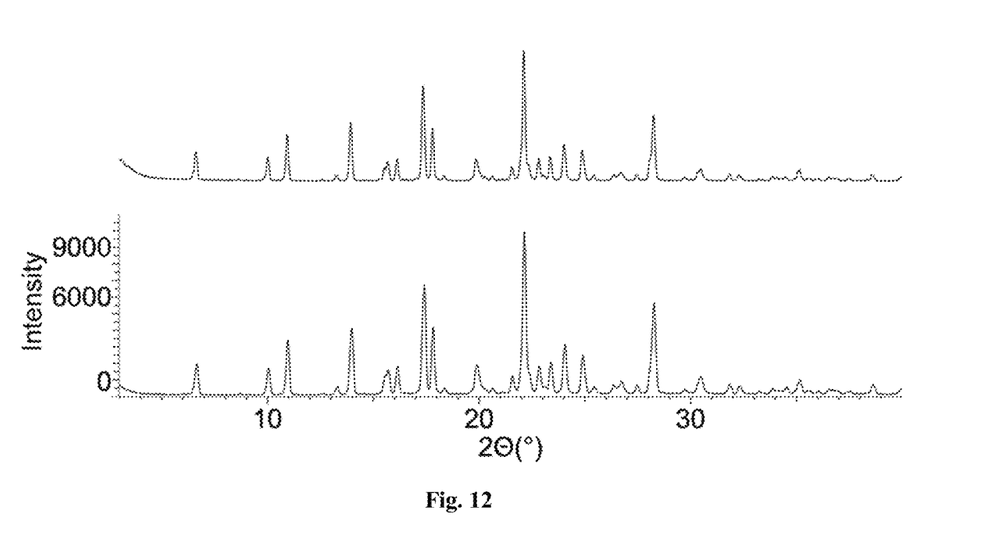
FIG. 12 shows the overlay of XRPD diagrams of Form A before (below) and after (above) DVS testing.

About 30 mg Form A of Compound I was assessed for hygroscopicity using a DVS analyzer, and tested by XRPD before and after DVS analysis. DVS is a gravimetric technique that measures how quickly and how much of a solvent is absorbed by a sample. The results showed that Form A had a water uptake of 0.14% under 80% RH, indicating that Form A is not hygroscopic (FIG. 11). The XRPDs of Form A did not change before and after DVS testing (FIG. 12).

Example 6. Stability Assessment of Form C

Figure 13:
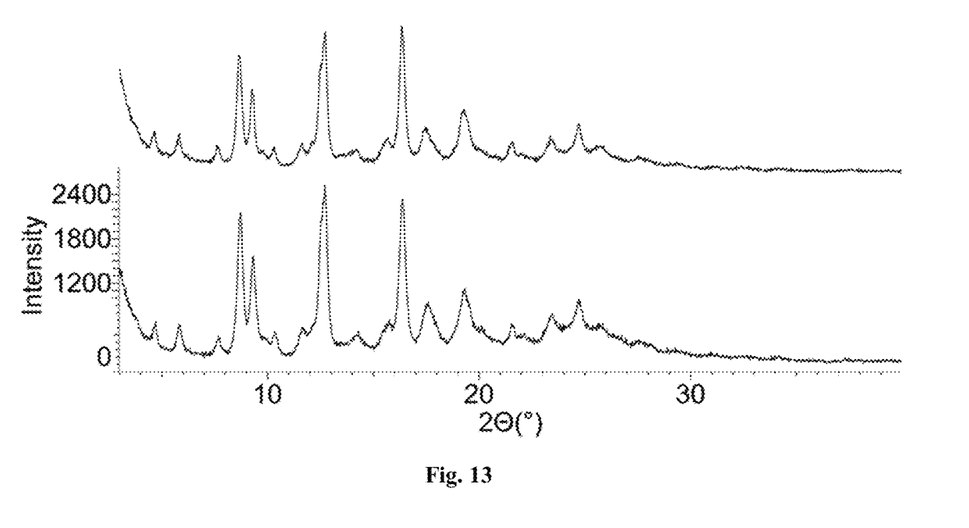
FIG. 13 shows the overlay of XRPD diagrams of Form C before (below) and after (above) stored under 25° C./60% RH for one week.
Figure 14:
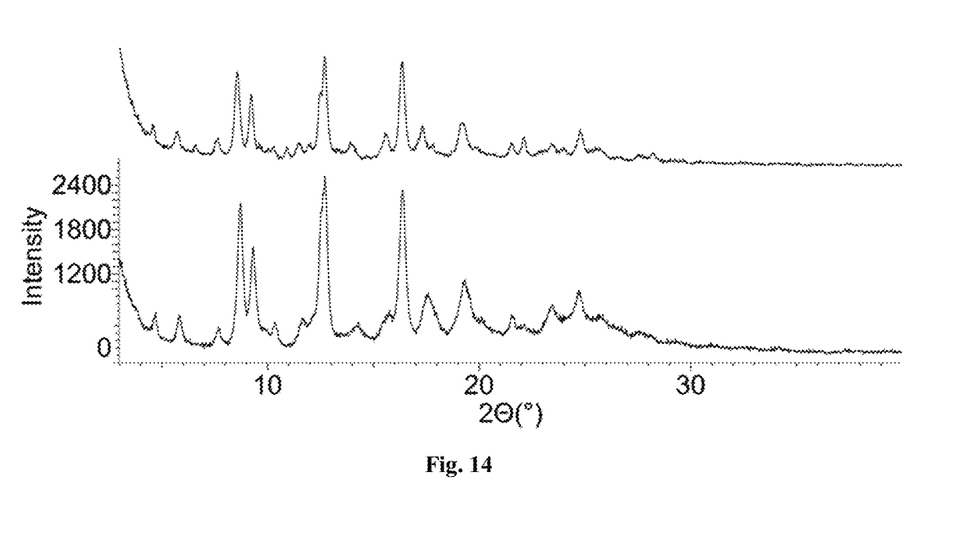
FIG. 14 shows the overlay of XRPD diagrams of Form C before (below) and after (above) stored under 40° C./75% RH for one week.

About 10 mg Form C of Compound I was added to each 1.5-mL glass vial and stored under 25° C./60% RH (FIG. 13) and 40° C./75% RH (opened, FIG. 14) for one week, and then analyzed for XRPD and HPLC purity. The XRPDs shown in FIGS. 13 and 14 have little or no change in the location of the characteristic peaks after one week. The stability results are shown in Table 5, indicating no significant purity change neither.

TABLE 1

| | Stability Testing Condition | | |
|---|---|---|---|
| | Day 0 | 25° C./60% RH for 1 week | 40° C./75% RH for 1 week |
| Purity (%) | 96.83 | 96.91 | 96.99 |
| Crystalline Form | C | C | C |

Example 7. Hygroscopicity Assessment of Form C

Figure 15:
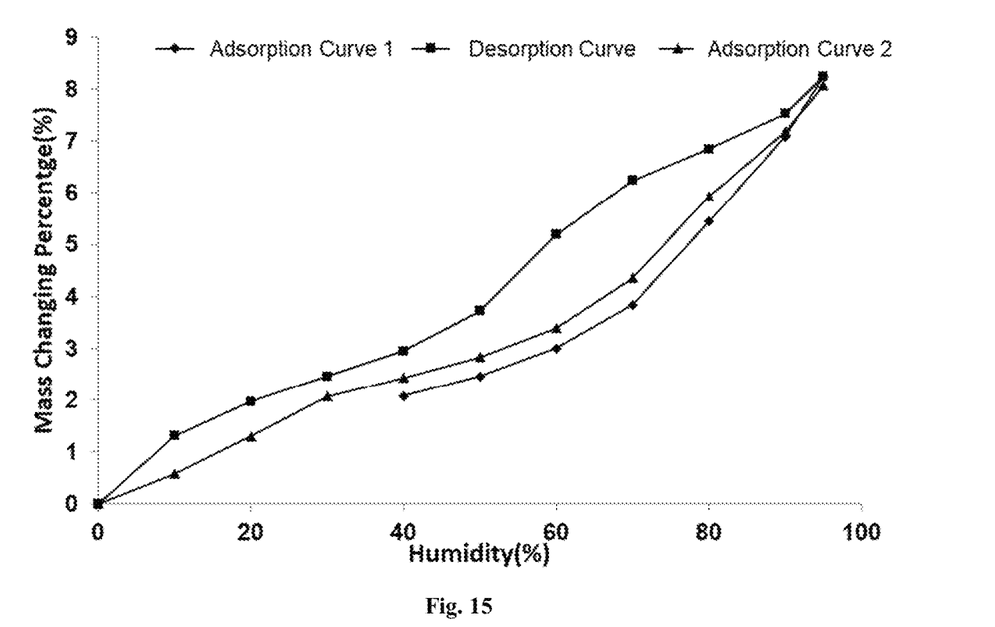
FIG. 15 shows a DVS diagram of Form C.
Figure 16:
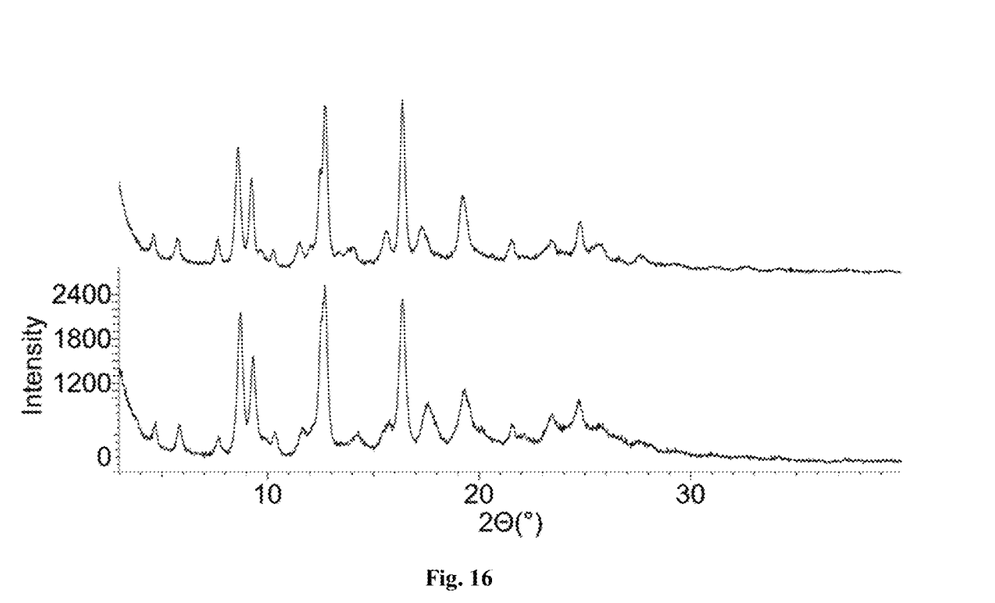
FIG. 16 shows the overlay of XRPD diagrams of Form C before (below) and after (above) DVS testing.

About 30 mg Form C of Compound I was assessed for hygroscopicity using a DVS analyzer, and tested by XRPD before and after DVS analysis. The results showed that Form C had a water uptake of 5.44% under 80% RH, indicating that Form C is moderately hydgroscopic (FIG. 15). The XRPDs of Form C did not change before and after DVS testing (FIG. 16).

Example 8. Interconversion of Forms A-C

Figure 17:
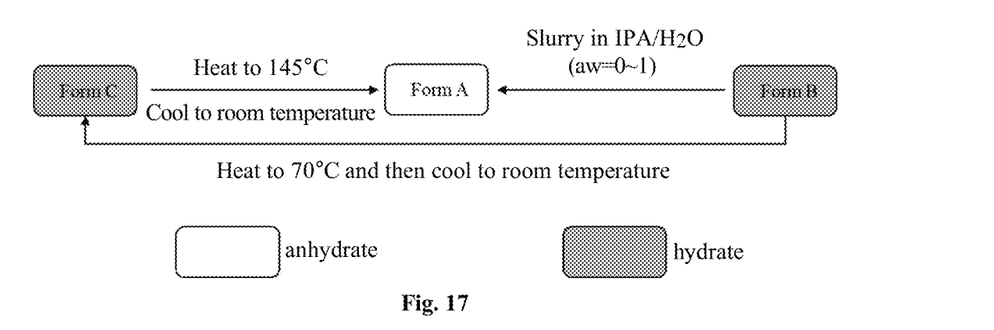
FIG. 17 shows interconversion of Forms A-C.

The relationships among Forms A-C were investigated via heating and slurry competition experiments. Form C was converted to Form A upon heating to 145° C. and subsequently cooling to room temperature. Slurry of a mixture containing equal amounts of Form A and B in solvent systems of isopropyl alcohol/water under different water activities ($a_w$=0~1) at room temperature gave Form A. Overall Form A has better thermodynamic stability at room temperature than Form B and C. The interconversion relationship is shown in FIG. 17.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A crystalline form of (S)-1-(1-acryloylpyrrolidin-3-yl)-3-((3,5-dimethoxyphenyl)ethynyl)-5-(methylamino)-1H-pyrazole-4-carboxamide having X-ray diffraction peaks at 22.1±0.2, 17.4±0.2, 28.3±0.2, 17.8±0.2, 14.0±0.2, degree 2theta, and wherein the most intense peak is at 22.1±0.2 degree 2theta.

2. A pharmaceutical composition comprising the crystalline form of claim 1 and a pharmaceutically acceptable carrier.

3. A crystalline form of (S)-1-(1-acryloylpyrrolidin-3-yl)-3-((3,5-dimethoxyphenyl)ethynyl)-5-(methylamino)-1H-pyrazole-4-carboxamide having X-ray diffraction peaks at 12.7±0.2, 16.4±0.2, 8.7±0.2, 9.3±0.2, 19.3±0.2, degree 2theta, and wherein the most intense peak is at 12.7±0.2 degree 2theta.

4. A pharmaceutical composition comprising the crystalline form of claim 3 and a pharmaceutically acceptable carrier.

5. A crystalline form of (S)-1-(1-acryloylpyrrolidin-3-yl)-3-((3,5-dimethoxyphenyl)ethynyl)-5-(methylamino)-1H-pyrazole-4-carboxamide having X-ray diffraction peaks at 9.0±0.2, 12.4±0.2, 19.3±0.2, 15.3±0.2, 11.5±0.2, 10.0±0.2, degree 2theta, and wherein the most intense peak is at 9.0±0.2 degree 2theta.

6. A pharmaceutical composition comprising the crystalline form of claim 5 and a pharmaceutically acceptable carrier.

* * * * *